(12) United States Patent
Okada et al.

(10) Patent No.: US 6,455,741 B1
(45) Date of Patent: Sep. 24, 2002

(54) PROCESS FOR PREPARING BENZOTHIOPHENECARBOXAMIDE DERIVATIVES

(75) Inventors: Tetsuo Okada, Sakai (JP); Makoto Kakinuma, Kaizuka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/133,319

(22) Filed: Apr. 29, 2002

Related U.S. Application Data

(62) Division of application No. 09/647,353, filed as application No. PCT/JP99/01617 on Mar. 30, 1999, now Pat. No. 6,399,788.

(30) Foreign Application Priority Data

Mar. 31, 1998 (JP) .......................................... 10-087311

(51) Int. Cl.$^7$ ............................................. C07C 209/36

(52) U.S. Cl. ...................................................... 568/705

(58) Field of Search ......................................... 568/705

(56) References Cited

FOREIGN PATENT DOCUMENTS

WO          98/25919          6/1998

OTHER PUBLICATIONS

P. Anelli et al., "Fast and Selective Oxidation of Primary Alcohols to Aldehydes or to Carboxylic Acids and of Secondary Alcohols to Ketones Mediated by Oxoammonium Salts under Two–Phase Conditions", J. Org. Chem., 1987; 52, pp. 2559–2562.

J. Ipaktschi, "Reduction of Oximes with Sodium Borohydride in the Presence of Transition Metal Compounds", Chem. Ber. 117, 1984, pp. 856–858 (abstract).

S. Kano et al., "Reduction of Some Functional Groups with Titanium(IV) Chloride/Sodium Borohydride", Synthesis, Sep. 1980, pp. 695–697.

K. Seno et al., "Thromboxane $A_2$ Receptor Antagonists. III. Synthesis and Pharmacological Activity of 6,6–Di–methyl-bicyclo[3.1.1]heptane Derivatives with a Substituted Sulfonylamino Group at C–2", Chem. Phar. Bull. vol. 37, No. 6, 1989, pp. 1524–1533.

T. Tsuri et al., "Bicyclo[2.2.1]heptane and 6,6–dimethylbi-cyclo[3.1.1]heptane derivatives: Orally active, potent, and selective prostagrandin D2 receptor antagonist", J. Med. Chem., (1997); 40(22), pp. 3504–3507.

*Primary Examiner*—T. A. Solola
(74) *Attorney, Agent, or Firm*—Wenderoth, Lind & Ponack, L.L.P.

(57) ABSTRACT

A process for preparing a compound having $PGD_2$ antagonism represented by the formula (I), or a pharmaceutically acceptable salt or hydrate thereof, which process comprises reacting an amino alcohol of the formula (II) or its salt with a compound of the formula (III) or its reactive derivative, oxidizing the product with halo oxoacid in the presence of 2,2,6,6-tetramethylpiperidine-1-oxyls, reacting the product with an ylide under the conditions for Wittig reaction, and optionally deprotecting the product.

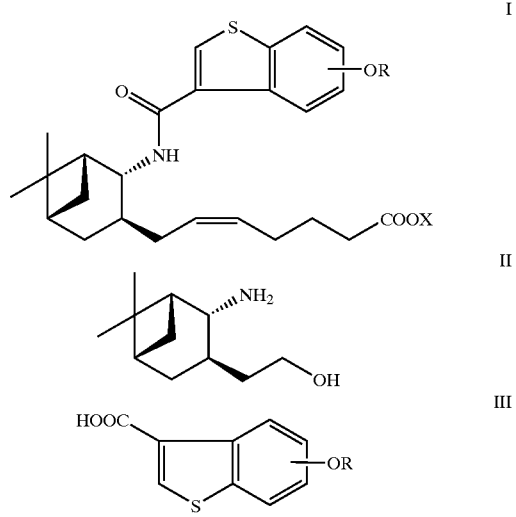

1 Claim, No Drawings

PROCESS FOR PREPARING BENZOTHIOPHENECARBOXAMIDE DERIVATIVES

This application is a divisional of Ser. No. 09/647,353 filed Sept. 29, 2000, now U.S. Pat. No. 6,399,788, which is a 371 of PCT/JP99/01617 filed Mar. 30, 1999.

TECHNICAL FIELD

The present invention relates to a process for producing benzothiophenecarboxamide derivatives useful as prostaglandin $D_2$ (hereinafter, referred to as "$PGD_2$") antagonists.

BACKGROUND ART

Benzothiphenecarboxamide derivatives of the general formula (I):

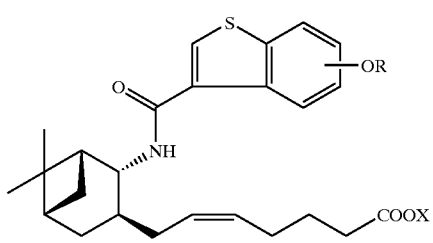

wherein R is hydrogen or a hydroxy-protecting group, X is hydrogen or alkyl, and double bond represents E or Z configuration are $PGD_2$ antagonists specific to $PGD_2$ receptors and useful as therapeutic agents for treating diseases associated with the dysfunction of the mast cell caused by excessive production of $PGD_2$ (WO97/00853, PCT/JP97/04527 (WO98/25919)). Consequently, the compound of the formula described above may be used as therapeutic agents for systemic mastocytosis, disorder of systemic mast cell activation, tracheal contraction, asthma, allergic rhinitis, allergic conjunctivitis, urticaria, injury due to ischemic reperfusion, inflammation, and atopic dermatis. Among them, a compound wherein OR is 5-hydroxy, X is hydrogen and double bond represents Z-configuration (hereinafter, referred to as "Compound A") possesses high antagonistic effect on $PGD_2$, showing especially high anti-nasal occlusion activity, and is contemplated to be a promising drug for treating nasal occlusion.

DISCLOSURE OF THE INVENTION

The compound (I) and processes for preparing the same have been known in literatures (WO97/00853, PCT/JP97/04527 (WO98/25919)). However, the known processes are not necessarily suited for industrial production in terms of production efficiency, safety for workers and environment and efficient use of resources because of the reasons exemplified as follows:

1) it uses silica gel chromatography unsuitable for mass production;
2) it is of low yield and time-consuming;
3) it involves complicated separation and purification processes of the reaction product;
4) it is accompanied by the generation of harmful gas, odor and/or waste fluid; and/or
5) it requires materials harmful or hard to handle as starting compounds, reagents, and/or solvents.

The present invention provides a process for preparing a compound of the formula (I):

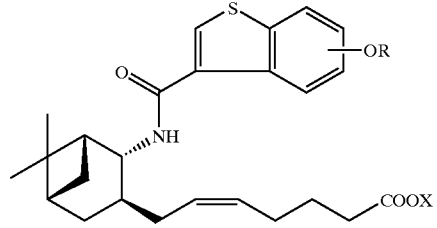

wherein R is hydrogen or a hydroxy-protecting group; X is hydrogen or alkyl; and double bond represents either E- or Z-configuration, or a pharmaceutically acceptable salt thereof or a hydrate thereof, which comprises reacting an amino alcohol of the formula (II):

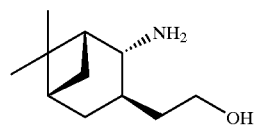

or a salt thereof with a compound of the formula (III):

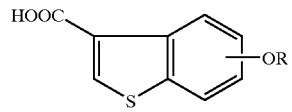

wherein R is hydrogen or a hydroxy-protecting group, or a reactive derivative thereof to yield a compound of the formula (I-2):

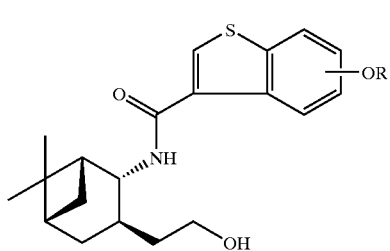

wherein R is as defined above; oxidizing the compound (I-2) with halo oxoacid in the presence of a compound of 2,2,6,6-tetramethylpiperidine-1-oxyls to yield a compound of the formula (I-3):

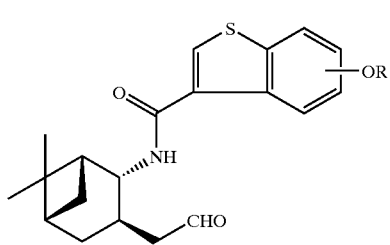

wherein R is as defined above; reacting the compound (I-3) with an ylide under the conditions for Wittig reaction and, if desired, deprotecting the reaction product.

THE BEST EMBODIMENT FOR PRACTICING THE INVENTION

In a preferred embodiment of the present invention, a compound of the formula (I-2):

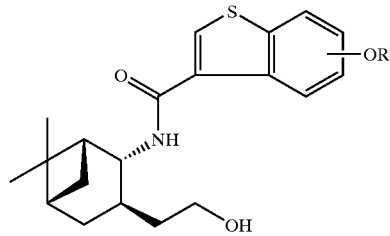

I-2 wherein R is as defined above is oxidized with halo oxoacid in the presence of 2,2,6,6-tetramethylpiperidine-1-oxyls to yield a compound of the formula (I-3):

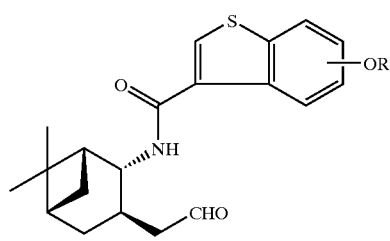

I-3 wherein R is as defined above.

In another preferred embodiment, a compound of the formula (II-2):

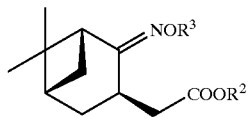

II-2 wherein $R^2$ is alkyl and $R^3$ is hydrogen or alkyl is reduced with reducing agent-Lewis acid system to yield an amino alcohol of the formula (II) or a salt thereof.

Preferably, the reducing agent used is selected from the group consisting of alkaline metal- or alkaline earth metal-substituted borohydrides; and the Lewis acid is selected from the group consisting of halide of tin, aluminum, titanium, boron, zirconium or nickel and complexes thereof with ethers.

In another preferred embodiment, a compound of the formula (II-2):

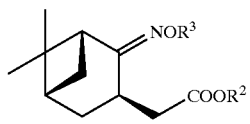

II-2 wherein $R^2$ and $R^3$ are as defined above is converted into an alcohol of the formula (II-3):

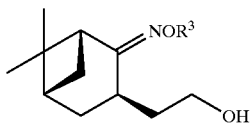

II-3 wherein $R^3$ is as defined above; and the alcohol is reduced with a reducing system of metal sodium-alcohol or reducing agent-Lewis acid to provide an amino alcohol of the formula (II) or a salt thereof.

The terms used herein are defined below.

The term "hydroxy-protecting group" means alkyl, alkoxyalkyl, acyl, aralkyl, alkylsulfonyl, arylsulfonyl, alkyl substituted silyl, alkoxycarbonyl, aryloxycarbonyl, aralkyloxycarbonyl or tetrahydropyranyl.

The term "alkyl" means $C_1$–$C_{20}$ linear or branched alkyl, particularly, methyl, ethyl, n-propyl, isopropyl, n-butyl, isobutyl, sec-butyl, tert-butyl, n-pentyl, isopentyl, neopentyl, tert-pentyl, hexyl, heptyl, octyl, nonyl, decyl, undecyl, dodecyl, tridecyl, tetradecyl, pentadecyl, hexadecyl, heptadecyl, octadecyl, nonadecyl and icosyl, and $C_1$–$C_6$ alkyl is preferred. As alkyl for $R^2$, $C_1$–$C_3$ alkyl is preferred.

The term "alkoxy" means $C_1$–$C_6$ linear or branched alkoxy, particularly, methoxy, ethoxy, n-propoxy, i-propoxy, n-butoxy, i-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy, t-hexyloxy and the like, and $C_1$–$C_3$ alkoxy is preferred.

The term "alkoxyalkyl" means alkyl group substituted by alkoxy group, including methoxymethyl, ethoxymethyl, methoxyethoxymethyl, ethoxyethyl, methoxypropyl and the like.

The term "acyl" means $C_1$–$C_{11}$, acyl derived from aliphatic carboxylic acid or aromatic carboxylic acid. Examples of aliphatic carboxylic acid-derived acyl include acetyl, chloroacetyl, trichloroacetyl, propionyl, butyryl, valeryl and the like, and examples of aromatic carboxylic acid-derived acyl include benzoyl, p-nitrobenzoyl, p-methoxybenzoyl, p-bromobenzoyl, toluoyl, naphthoyl and the like.

The term "aryl" means phenyl, naphthyl or polycyclic aromatic hydrocarbon group and the like. In addition, aryl may be substituted by the following substituents.

Examples of substituent include alkyl such as methyl, ethyl, n-propyl, isopropyl, isobutyl, sec-butyl, tert-butyl, n-pentyl, isopentyl, neopentyl or tert-pentyl, lower alkoxy such as methoxy or ethoxy, halogen such as fluoro, chloro, bromo or iodo, nitro, hydroxy, carboxy, cyano, sulfonyl, amino, lower alkylamino such as methylamino, dimethylamino, ethylmethylamino or diethylamino, and the like. The aryl group may have one or more substituents at any possible positions. Specific examples of aryl include 2-methylphenyl, 3-methylphenyl, 4-methylphenyl, 2-ethylphenyl, 3-ethylphenyl, 4-ethylphenyl, 4-pentylphenyl, 4-carboxyphenyl, 4-acetylphenyl, 4-(N,N-dimethylamino)phenyl, 4-nitrophenyl, 4-hydroxyphenyl, 4-methoxyphenyl, 4-fluorophenyl, 4-chlorophenyl, 4-iodophenyl and the like.

The aryl group in the "aralkyl", "arylsulfonyl", "aryloxycarbonyl" or "aralkyloxycarbonyl" described below may have similar substituents as defined above.

The term "aralkyl" means an alkyl group substituted by aryl group, and includes benzyl, 4-methylbenzyl, 4-methoxybenzyl, 3,4-dimethoxybenzyl, naphthylmethyl, phenethyl, and the like.

The term "alkylsulfonyl" means a sulfonyl group substituted by alkyl group, and includes methanesulfonyl, ethanesulfonyl and the like.

The term "arylsulfonyl" means a sulfonyl group substituted by aryl group, and includes benzenesulfonyl, p-toluenesulfonyl, and the like.

The term "alkyl-substituted silyl" means mono-, di- or tri-alkyl-substituted silyl, for example, methylsilyl, dimethylsilyl, trimethylsilyl, t-butyldimethylsilyl, and the like.

The term "alkoxycarbonyl" means methoxycarbonyl, isopropoxycarbonyl, t-butoxycarbonyl, and the like.

The term "aryloxycarbonyl" means phenoxycarbonyl, and the like.

The term "aralkyloxycarbonyl" means benzyloxycarbonyl, and the like.

As hydroxy-protecting group represented by R, the above-mentioned alkyl, alkoxyalkyl, acyl, aralkyl, alkylsulfonyl, arylsulfonyl, alkyl-substituted silyl, alkoxycarbonyl, aryloxycarbonyl, aralkyloxycarbonyl or tetrahydropyranyl are preferred and aryl sulfonyl is more preferred.

Examples of salts of a compound of the general formula (I) include alkali metal salts such as lithium salt, sodium salt or potassium salt and the like, alkali earth metal salts such as calcium salt and the like, ammonium salt, salts with organic base such as tromethamine, trimethylamine, triethylamine, 2-aminobutane, tert-butylamine, diisopropylethylamine, n-butylmethylamine, n-butyldimethylamine, tri-n-butylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthalenemethylamine, diphenylbenzylamine, triphenylamine, 1-naphthylamine, 1-aminoanthracene, 2-aminoanthracene, dehydroabiethylamine, N-methylmorpholine or pyridine, or amino acid salts such as lysine salt or arginine salt.

The salts of amino alcohols of the formula (II) include salts with organic acid such as benzoic acid, etc., and mineral acid such as hydrochloric acid, sulfuric acid, etc.

The objective compound of the present invention is illustrated by the general formula (I), in which the double bond of the alkenylene side chain (i.e., 5-heptenylene chain) may be in E- or Z-configuration.

The method of the present invention is described below in more detail. When a substituent(s) possibly interfering the reaction exists, it may be appropriately protected and deprotected at a desired stage. Such protection or deprotection can be accomplished by a procedure known in the art.

I. Preparation of Compound (I)

Scheme I

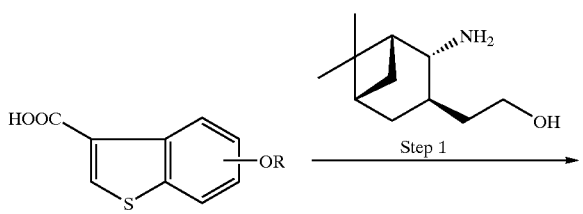

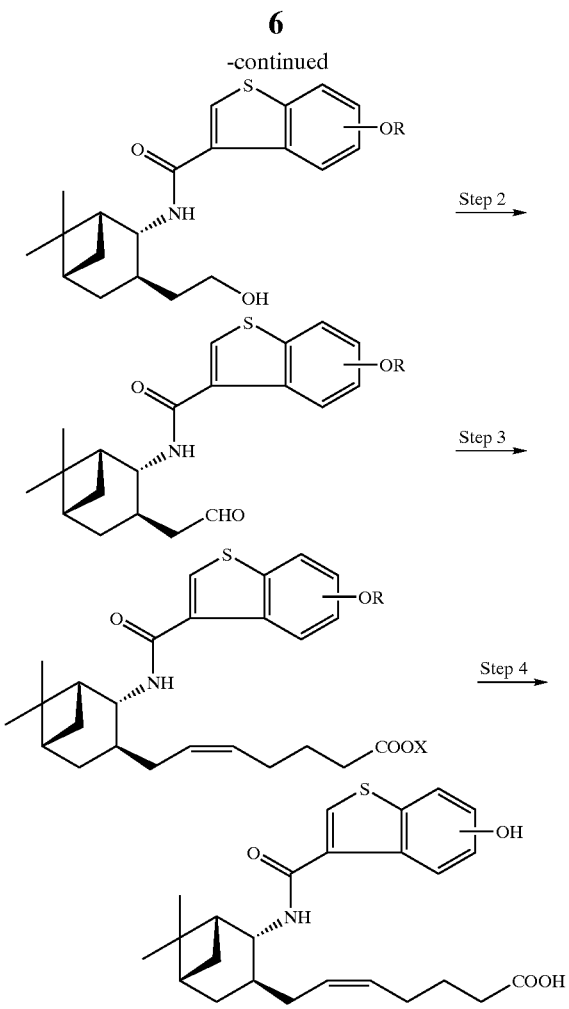

wherein R and X are as defined above.

[Step 1]

This step is related to the preparation of amide (I-2) by acylating an amino alcohol (II) or a salt thereof with carboxylic acid (III) or a reactive derivative thereof.

The carboxylic acid (compound III) used in the acylation can be synthesized by a method known in literatures [for example, Nippon-Kagaku Zasshi vol. 88, No. 7, 758–763 (1967); Nippon-Kagaku Zasshi vol. 86, No. 10, 1067–1072 (1965); J. Chem. Soc. (C). 1899–1905 (1967); J. Heterocycle. Chem. vol. 10, 679–681 (1973)]. The term "reactive derivative" of carboxylic acid (III) refers to corresponding acid halides (e.g., chloride, bromide, iodide), acid anhydrides (e.g., mixed acid anhydride with formic acid or acetic acid), activated esters (e.g., succinimide ester), and the like, and includes acylating agents generally used for the acylation of amino group. For example, to obtain acid halides, a carboxylic acid is reacted with thionyl halide (e.g., thionyl chloride), phosphorous halide (e.g., phosphorous trichloride, phosphorous pentachloride), oxalyl halide (e.g., oxalyl chloride), or the like, according to a known method (e.g., Shin-jikken Kagaku Koza, vol. 14, p. 1787 (1978); Synthesis 852–854 (1986); Shin-jikken Kagaku Koza vol. 22, p. 115 (1992)).

The acylation can be carried out under ordinary conditions used for the acylation of amino group. For example, when a carboxylic acid halide is used, the reaction is carried out according to a method commonly known as "Schotten-Baumann reaction". In general, carboxylic acid halide is added dropwise to an aqueous alkaline solution of amine with stirring and under cooling while removing the generating acid with alkali. Alternatively, when a carboxylic acid is used as a free acid not a reactive derivative, the reaction can be conducted conventionally in the presence of a coupling agent generally used in the coupling reaction between an amine and a carboxylic acid such as dicyclohexylcarbodiimide (DCC), 1-ethyl-3-(3-dimethylaminopropyl)-carbodiimide or N,N'-carbonyldiimidazole.

[Step 2]

This step is related to the oxidation of an alcohol (I-2) to an aldehyde (I-3). Hitherto such reaction has been conducted by using an oxidizing agent of chromic acid series such as Jones reagent (J. Org. Chem., 40, 1664–1665 (1975)), Collins reagent (J. C. S. Chem. Comm., 1972 1126) or pyridinium chlorochromate (Tetrahedron Lett., 2647–2650 (1975)). Further, methods wherein manganese dioxide (Helv. Chim. Acta., 39, 858–862 (1956)) or dimethyl sulfoxide (Swern oxidation, J. Org. Chem., 43, 2480–2482 (1978)) have been known. However, these existing methods have disadvantages. For example, chromic acids are toxic to human body and,must be detoxified after use. Further, the Swern oxidation using dimethyl sulfoxide-oxalyl chloride is not suited for a large scale production because it is accompanied by the generation of carbon monoxide harmful to workers and sulfurous odor and also it must be carried out at low temperature, for example, between −50° C. and −78° C.

According to the method of the present invention, alcohol (I-2) is oxidized with an oxidizing agent(s) such as halo oxoacid in the presence of 2,2,6,6-tetramethylpiperidine-1-oxyls (referred to as "TEMPOs") as described in a literature (e.g., J. Org. Chem., 52, 2559–2562 (1987)), whereby the problems of existing methods are solved. Examples of TEMPO include 2,2,6,6-tetramethylpiperidine-1-oxyl, 4-methoxy-2,2,6,6-tetramethylpiperidine-1-oxyl, 4-acetylamino-2,2,6,6-tetramethylpiperidine-1-oxyl, 4-benzoyloxy-2,2,6,6-tetramethylpiperidine-1-oxyl, and 4-cyano-2,2,6,6-tetramethylpiperidine-1-oxyl. Examples of halo oxoacid include sodium hypochlorite, sodium hypobromite, sodium bromite and higher bleaching powder. A solution of an oxidizing agent may be adjusted to, for example, pH 8.5 to 9.5 with a mineral acid such as sodium hydrogen carbonate, hydrochloric aci or sulfuric acid. Alternatively, a solution of an oxidizing agent may be added in the presence of sodium hydrogen carbonate. The reaction can be accomplished within several minutes to several tens minutes at temperature from ice-cooling to room temperature in a solvent such as ethyl acetate, acetonitrile or dichloromethane.

The advantageous characteristics of the new oxidation method of the present invention are as follows:

1) the process requires simple operations and short period of time since the reaction renders a product at high yield within short reaction time without keeping very lower temperature;

2) the process is safe since the reaction solvent used are water and ethyl acetate;

3) the separation and purification of reaction products can be conducted only by extraction;

4) the oxidation is carried out with a cheap reagent, sodium hypochlorite, with only a quite small amount of catalyst, TEMPO, at 1–0.2% molar equivalent to alcohol (I-2);

5) it allows the operators to work in better environment because the reaction generates little carbon monoxide or odor in contrast with Swern oxidation, and, further, sodium chloride resulting from sodium hypochlorite used in the oxidation is unnecessary to be detoxified.

[Step 3]

This step is related to the formation of a double bond by reacting a compound of the formula (I-3) with an ylide $(Ph_3P=CH(CH2)_3COOH)$. The reaction for providing a double bond can be carried out in a conventional manner for Wittig reaction. The ylides used in the reaction can be synthesized, in the presence of a base, by treating a phosphonium salt which has been synthesized from triphenylphosphine and an alkyl halide having a desired alkyl group to be condensed, for example, 5-bromopentanoic acid. Examples of a base include dimsyl sodium, dimsyl potassium, sodium hydride, n-butyl lithium, potassium t-butoxide and lithium diisopropylamide. The reaction is accomplished within several hours at room temperature in a solvent such as ether, tetrahydrofuran, n-hexane, 1,2-dimethoxyethane or dimethyl sulfoxide.

[Step 4]

In this step, a compound (I) wherein R is hydroxyprotecting group is deprotected to provide compound (I-1). The reaction can be carried out in a conventional manner using, as a catalyst, hydrochloric acid, sulfuric acid, sodium hydroxide, potassium hydroxide or barium hydroxide, or the like. The reaction is accomplished within several tens minutes to several hours with heating in a solvent such as methanol-water, ethanol-water, acetone-water, acetonitrile-water, or the like, preferably dimethyl sulfoxide-water. The OR may be positioned at any of 4-, 5-, 6- and 7-positions though, it is preferred to be at 5-position.

II. Preparation of Compound (II)

The starting material in this process, amino alcohol (II), can be prepared by a known procedure starting from, for example, (−)-myrtenol. A precursor, methoxime ester of the formula (II-2) wherein $R^3$ is methyl, is then reduced with metal sodium in isopropanol to give the corresponding amino alcohol (II) (Hagishita, et al., Chem. Pharm. Bull., 37 (6), 1524–1533 (1989)). However, this method have problems such as low yield (39.6%) or poor selectivity.

As reducing agents used in the reduction of esters to alcohols, there have been known sodium borohydride (J. Org. Chem., 28, 3261 (1982)), lithium aluminum hydride (Org. Syn., 63, 140), lithium borohydride (J. Org. Chem., 47, 4702 (1982)) and the like. Further, as methods for reducing oximes to amines, there have been known catalytic reduction (Syn. Comm., 27, 817 (1997); Org. Syn., coll. vol. 5, 376 (1973)) or methods which use a reducing agent(s) such as diborane (J. Org. Chem., 30, 2877 (1965)), sodium borohydride (J. Org. Chem., 48, 3412 (1983)), lithium aluminum hydride (Tetrahedron, 51, 8363 (1995)), sodium borohydride-titanium chloride (IV) (Synthesis. 1980 695), sodium borohydride-nickel chloride (II) (Chem. Ber., 117, 856 (1984)), or the like. None of the literatures above, however, do not teach a method for reducing both ester and oxime moieties present in one molecule such as a compound of the formula (II-2) simultaneously in high yield with high stereoselectivity.

The present inventors have succeeded in reducing oxime ester of the formula (II-2) to the objective amino alcohol (II) in high yield with high selectivity by using a reducing agent-Lewis acid system (especially, sodium borohydride-Lewis acid) as shown in Scheme II below.

Scheme II

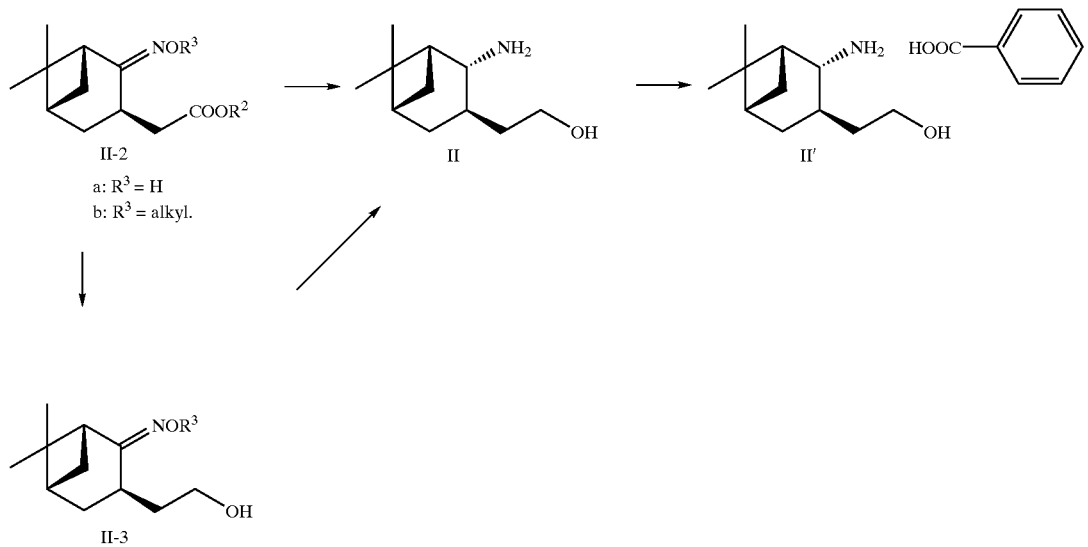

II-2
a: $R^3$ = H
b: $R^3$ = alkyl.

wherein $R^2$ and $R^3$ are as defined above.

According to the present process, an oxime ester (II-2) is reduced directly or via alcohol (II-3) to give an amino alcohol (II) or a salt thereof. Reducing agents usable in the reaction above include alkali metal- or alkaline earth metal-substituted borohydrides (sodium borohydride, lithium borohydride, calcium borohydride, etc.).

Examples of Lewis acid include halides of tin, aluminium, boron, titanium, zirconium or nickel (e.g., stannous chloride, stannic chloride, aluminium chloride, titanium tetrachloride, boron trifluoride, zirconium tetrachloride, nickel dichloride, etc.) or a ether complexes thereof (e.g., sodium bis(2-methoxyethoxy)aluminium hydride, etc.).

Examples of solvent include ethers (e.g., ethyl ether, tetrahydrofuran, 1,2-dimetoxyethane, dioxane, diethylene glycol dimethyl ether, etc.), hydrocarbons (e.g., toluene, xylene, etc.), and a mixed solvents between ethers and hydrocarbons. Regarding the reduction of an alcohol (II-3) to an amino alcohol (II) or its salt, a method which uses metal sodium-alcohol is also availabe in addition to the above-mentioned reducing agent-Lewis acid system. Examples of alcohol include methanol, ethanol, n-propanol, i-propanol, and the like. Examples of solvents include hydrocarbons (e.g., toluene, xylene, etc.) The process for reaction will be described concretely below. The raw material, oxime ester (or alkyl-substituted oxime) (II-2a or II-2b) is dissolved in 2 volumes or more of a solvent. To the solution are added 2 or more molar equivalents of a reducing agent and then a Lewis acid at 0.1 to 0.4 molar equivalents to the reducing agent at 0° C. to 150° C. Alternatively, a mixture previously prepared by combining a Lewis acid and a solvent may be added. Further, the order for adding a raw material, an oxime ester, a reducing agent and a Lewis acid can be changed. The reaction mixture is then treated at 0° C. to 150° C. for several minutes to several hours for reaction. The reaction solution can be worked up by adding water and dilute mineral acid (e.g., dilute hydrochloric acid) followed by stirring, whereby the reducing agent is destroyed. Alternatively, the reaction solution may be poured into dilute mineral acid.

The solution is then neutralized with an alkali (e.g., sodium hydroxide) and extracted with an organic solvent (e.g., ethyl acetate). When the solvent is distilled off, an amino alcohol (II) is obtained. If necessary, the product can be further purified by converting into a crystalline salt (II') with an appropriate acid (e.g., benzoic acid) and then neutralizing with an alkali to give amino alcohol (II).

According to the above-mentioned process of the present invention, the objective amino alcohol (II) can be prepared in high yield (about 89%) with high stereoselectivity (99% or more).

Although the process for preparing a compound of the formula (II) shown in the scheme II above is novel and useful for the preparation of a compound (II) in itself, it also contributes to establish safe and efficient production of a compound (I), the final product, when combined with a process for preparing the compound (I).

The following Examples are provided to further illustrate the present invention in more detail and should not be interpreted in any way as to limit the scope thereof. The abbreviations used in the Examples have the following meanings:

Ph: phenyl
Ac: acetyl
TEMPO: 2,2,6,6-tetramethylpiperidine-1-oxyl

Reference Example 1

Preparation of ethyl [(1R, 3R, 5S)-2-methylidene-10-norpinan-3-yl]acetate (2)

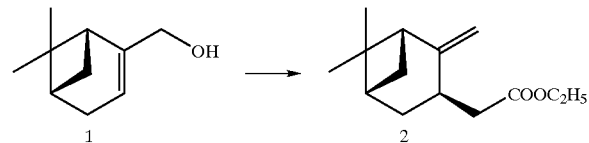

The mixture of (−)-myrtenol (1) (6.44 g, 42.3 mmol), triethyl orthoacetate (23 ml, 126 mmol) and hydroquinone (27 mg) was heated with stirring at 165° C. for 2 hours, at 185° C. for 2 hours and at 195° C. for 25 hours, and the resulting ethanol was distilled off. The resulting oil was purified by chromatography on silica gel (hexane:toluene= 10:0–1:1) to provide 7.66 g of the title compound (2). Yield: 81.4%.

IR (Film): 3070, 2980, 2921, 2869, 1737, 1638 cm$^{-1}$ $^1$H NMR δ(CDCl$_3$), 300 MHz: 0.76 and 1.24 (each, 3H, each, s), 1.20 (1H, d, J=9.9 Hz), 1.27 (3H, t, J=7.2 Hz), 1.52 (1H, m), 2.00 (1H, m), 2.23–2.50 (3H, m), 2.66 (1H, dd, J=5.1 and 15.3 Hz), 3.03 (1H, m), 4.16 (2H, q, J=7.2 Hz), 4.71 (2H, d, 11.4 Hz)

Elemental Analyses for C$_{14}$H$_{22}$O$_2$

Calculated (%):C, 75.63; H, 9.97

Found (%): C, 75.61; H, 9.99

$[α]_D^{24}$+29.1° (c=1.05, CH$_3$OH)

Reference Example 2

Preparation of 5-benzenesulfonyloxybenzo[b]thiophene-3-carbonyl chloride (6)

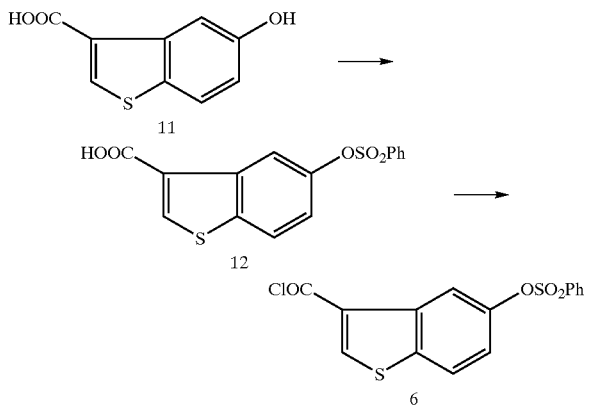

5-Hydroxybenzo[b]thiophene-3-carboxylic acid (11) (M.Martin-Smith et al. J. Chem. Soc (C), 1899–1905 (1967) 8.63 g (44.4 mmol)) was dissolved in aqueous tetrahydrofuran (water content, 20%; 160 ml) and 1 N sodium hydroxide (44 ml). To the solution were added dropwise 0.56 N sodium hydroxide (87 ml) and benzenesulfonyl chloride (6.2 ml, 48.4 mmol) simultaneously with stirring under ice-cooling while maintaining the pH at 11–12. After the completion of the reaction, the mixture was diluted with water, basified, and washed with toluene. The aqueous layer was made slightly acidic by adding concentrated hydrochloric acid with stirring, and the deposited crystals were filtered, washed with water and dried to provide 14.33 g of 5-benzenesulfonyloxybenzo[b]thiophene-3-carboxylic acid (12). M.p. 202–203° C.

NMR δ(CDCl$_3$), 300 MHz: 7.16 (1H, dd, J=2.7 and 9.0 Hz), 7.55–7.61 (2H, m), 7.73 (1H, m), 7.81 (1H, d, J=9.0 Hz), 7.90–7.94 (2H, m), 8.16 (1H, d, J=2.7 Hz), 8.60 (1H, s).

IR (Nujol): 3102, 2925, 2854, 2744, 2640, 2577, 1672, 1599, 1558, 1500, 1460, 1451 cm$^{-1}$ Elemental Analyses for C$_{15}$H$_{10}$O$_5$S$_2$ Calculated (%):C, 53.88; H, 3.01; S, 19.18

Found (%): C, 53.83; H, 3.03; S, 19.04

The 5-benzenesulfonyloxybenzo[b]thiophene-3-carboxylic acid (12) (5.582 g, 16.7 mmol) prepared above was refluxed with dimethylformamide (1 drop), thionyl chloride (3.57 ml, 50 mmol) and toluene (22 ml) for 1.5 hours. When the solvent was removed under reduced pressure, 5.89 g of the objective compound (6) was obtained.

EXAMPLE 1

Preparation of Amino Alcohol (1) Step 1

Preparation of Ethyl [(1R, 3R, 5S)-2-oxo-10-norpinan-3-yl]acetate (3)

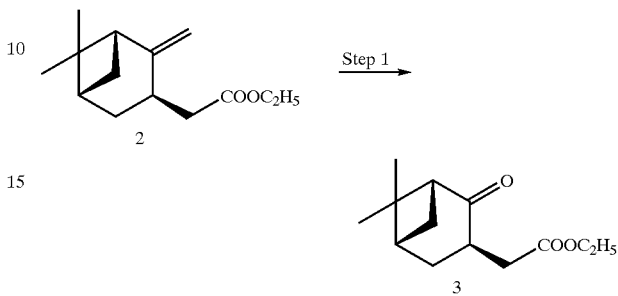

The compound (2) (333.5 g, 1.5 mol) prepared in Reference Example 1 was dissolved in dichloromethane (3.340 L) and methanol (660 ml). The mixture was cooled to −70 to −73° C. and ozone gas was introduced for 4 hours. After introducing nitrogen gas for 1 hour, trimethyl phosphite (265 ml, 2.26 mol) was added and the reaction was allowed to warm to room temperature. The reaction mixture was partitioned into two layers by adding ice-water (150 ml) and 10% sulfuric acid (300 g). The organic layer was sequentially washed with water (1.2 L), 82% sodium sulfite (1.2 Kg) and water (1.2 L). The aqueous layer was extracted with ethyl acetate (1.11 L). The organic layers were combined and the solvent was distilled off under reduced pressure to provide 456.51 g of oil, which was then dissolved in tetrahydrofuran (1.01 L). After adding cold 14% aqueous ammonium hydroxide (106.8 g), the resulting pale yellow solution was stirred at room temperature for 1 hour. The reaction mixture was diluted with ice-water (750 ml). After adding ethyl acetate (1.1 L), the mixture was stirred and partitioned into layers. The same procedures were repeated once more and the aqueous layer was further extracted with ethyl acetate. The combined organic layer was washed with 10% brine (750 ml), dried over anhydrous magnesium sulfate and then the solvent was distilled off under reduced pressure. The resulting oil was dissolved in toluene (500 ml) and the solvent was distilled off under reduced pressure to provide 347.96 g of oil. Crude yield: 103.4%.

$^1$H NMR δ(CDCl$_3$), 300 MHz; 0.95 and 1.34 (each 3H, each s), 1.27 (3H, t, J=7.0 Hz), 1.40 (1H, d, J=9.9 Hz), 1.67 (1H, m), 2.25 (1H, m), 2.33–2.42 (2H, m), 2.56–2.65 (2H, m), 2.86–3.02 (2H, m), 4.14–4.21 (2H, m)

(2) Step 2

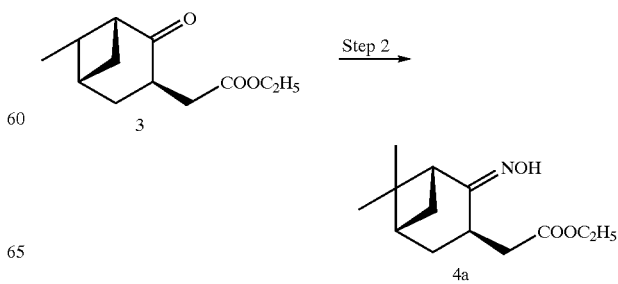

1) Preparation of Ethyl [(1R, 3R, 5S)-2-hydroxyimino-10-norpinan-3-yl]acetate (4a)

The compound (3) (10.05 g, 44.9 mmol) was dissolved in ethanol (45 ml). To the solution were added hydroxylamine hydrochloride (4.99 g, 71.9 mmol) and pyridine (4.7 ml, 58.1 mmol) and the mixture was heated at 60° C. for 2.5 hours with stirring. The reaction mixture was concentrated under reduced pressure, diluted with water and acidified with hydrochloric acid, and then extracted with ethyl acetate. The organic layer was sequentially washed with water, aqueous sodium hydrogen carbonate and water, dried over anhydrous magnesium sulfate and the solvent was then distilled off under reduced pressure to provide 10.72 g of the title compound (4a) as colorless oil. Crude yield: 100%.

$[\alpha]_D^{24}+55.3°$ (c=1.01, CH$_3$OH)

2) Preparation of Ethyl [(1R, 3R, 5S)-2-methoxyimino-10-norpinan-3-yl] acetate (4b)

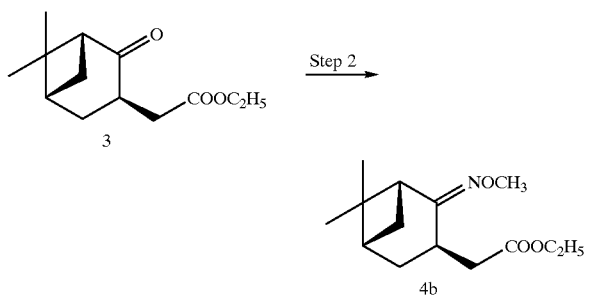

The compound (3) (107.0 g, 477 mmol) was dissolved in ethanol (500 ml). To the solution were added O-methylhydroxylammonium chloride (50.1 g, 600 mmol) and pyridine (47.5 g, 600 mmol) and the mixture was refluxed for 3 hours with stirring. The reaction mixture was concentrated under reduced pressure, diluted with water, acidified with hydrochloric acid and then extracted with ethyl acetate. The organic layer was sequentially washed with water, aqueous sodium hydrogen carbonate and water, dried over anhydrous magnesium sulfate and then the solvent was distilled off under reduced pressure. The resulting colorless oil was distilled under reduced pressure to provide 106.1 g of the title compound (4b). Boiling point 118–123° C. (reduced pressure 1.2 mmHg). Yield: 87.8%.

IR (Film): 1738, 1630 cm$^{-1}$

Elemental Analyses for C$_{14}$H$_{23}$NO$_3$

Calculated (%):C, 66.37; H, 9.15; N, 5.53

Found (%): C, 65.92; H, 9.13; N, 5.60

$[\alpha]_D^{24}+69.5°$ (c=1.00%, CH$_3$OH)

(3) Step 3

Preparation of [(1R, 2R, 3R, 5S)-2-amino-10-norpinan-3-yl]ethanol benzoic acid salt (II')

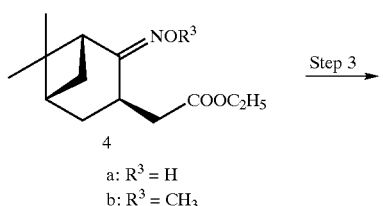

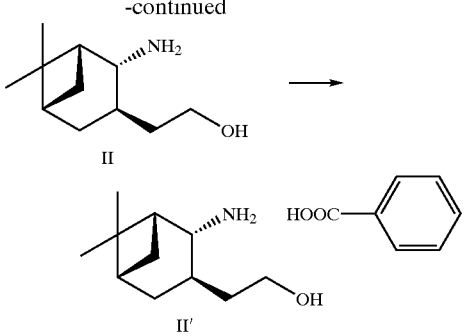

1) Preparation from a Compound (4b)

Sodium borohydride (799 mg, 21.1 mmol) was suspended in 1,2-dimethoxyethane (5 ml). To the suspension were added with stirring under ice-cooling a suspension of aluminum chloride (507 mg, 3.8 mmol) in 1,2-dimethoxyethane (5 ml) followed by a solution of the compound (4b) (1.07 g, 4.2 mmol) in 1,2-dimethoxyethane (3 ml), and the mixture was warmed in a bath at 70° C. for 3 hours. To the reaction were sequentially added water (4 ml), 2 hydrochloric acid (8 ml) and concentrated hydrochloric acid (1 ml) with stirring under ice-cooling, and the mixture was then stirred at room temperature for 40 minutes. The reaction was washed with ether, neutralized with sodium hydroxide and extracted with ethyl acetate. The organic layer was dried over anhydrous magnesium sulfate and the solvent was then distilled off under reduced pressure to provide 789 mg of title compound (II) as colorless oil. The product was dissolved in ethyl ether (5 ml). To the solution was added a solution of benzoic acid (516 mg, 4.2 mmol) in ether (5 ml), and the mixture was stirred. The deposited crystals were filtered and washed with ether and dried to provide 1.146 g of colorless benzoic acid salt of amino alcohol (II'). Yield: 89% (purity: 99.2%), mp 183–185° C. The purity of the benzoic acid salt of amino alcohol (III) was measured by converting the salt into benzamide in the presence of a condensing agents such as dicyclohexylcarbodiimide (DCC) and 1-hydroxybenztriazole (HOBT) in tetrahydrofuran, and determining the purity of the resulting amide using high performance liquid chromatography (HPLC).

IR (KBr): 3420, 2600 (br), 1621, 1523, 1386 cm$^{-1}$ $^1$H NMR δ(CDCl$_3$): 300 MHz; 0.72 (1H, d, J=9.9 Hz), 1.06 and 1.13 (each 3H, each s), 1.40 (1H, m), 1.56–1.92 (3H, m), 2.12–2.36 (4H, m), 3.29 (1H, m), 3.62 (1H, m), 3.78 (1H, m), 7.32–7.47 (3H, m), 7.97–8.04 (2H, m)

| Elemental Analyses for C$_{18}$H$_{27}$NO$_3$ | |
|---|---|
| Calculated (%): | C, 70.79; H, 8.91; N, 4.59. |
| Found (%): | C, 70.54; H, 8.93; N, 4.56. |

$[\alpha]_D^{25}+27.6°$ (c=1.00%, CH$_3$OH)

Reference values: mp 180–183° C., $[\alpha]_D^{26}+27.1°$ (Chem. Pharm. Bull., 37, 1524 (1989))

[HPLC conditions] apparatus; LC-6A type (Shimazu) column: YMC-pack ODS-AMAM-302 (4.6 mmφ×150 mm); flow rate: 1.0 ml/min; detection: UV 254 nm; mobile phase: acetonitrile/water(1:1); retention time: 5.23 minutes

2) Preparation from a Compound (4a) (part 1)

Sodium borohydride (1.55 g, 41.0 mmol) was suspended in diethylene glycol dimethyl ether (13 ml). To the suspension was added boron trifluoride etherate (1.71 ml, 13.5 mmol) with stirring under ice-cooling over 10 minutes, and the mixture was stirred at room temperature for 20 minutes. After addition of a solution of compound (4a) (1.015 g, 4.1 mmol) in diethylene glycol dimethyl ether (8 ml), the mixture was stirred at room temperature for 20 minutes. The mixture was then heated in a bath at 110° C. with stirring for 2 hours. The solution was treated as described in above 1) to provide 741 mg of benzoic acid salt of amino alcohol (II'). Yield: 59% (purity: 99.2%), mp 178–180° C.

3) Preparation from a Compound (4a) (Part 2)

Sodium borohydride (1.00 g, 26.4 mmol) was suspended in 1,2-dimethoxyethane (10 ml). To the suspension were added compound (4a) (1.00 g, 4.03 mmol) and titanium tetrachloride-1,2-dimethoxyethane complex (1:1) (700 mg, 2.51 mmol) with stirring under ice-cooling. The mixture was stirred at room temperature for 30 minutes and, furthermore, heated in a bath at 70° C. with stirring for 3 hours. The mixture was treated as described in above 1) to provide 750 mg of benzoic acid salt of amino alcohol (II'). Yield: 61% (purity: 94.2%), mp 176–180° C.

(4) Step 4

Preparation of [(1R, 3R, 5S)-2-methoxyimino-10-norpinan-3-yl]ethanol (5)

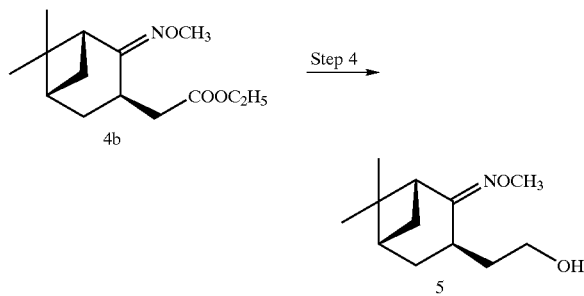

The compound (4b) (23.8 g, 94 mmol) was dissolved in toluene (111 ml). To the solution was added a solution of 70% sodium bis(2-methoxyethoxy)aluminum hydride in toluene (34.4 g, 119 mmol) at temperature below 25° C. over 20 minutes, and stirring was continued for 30 minutes at the same temperature. To the reaction mixture was added acetone (7 g) to decompose the reagent, followed by water (30 ml) and then 48% sodium hydroxide (43.8 g). The resulting two layers were separated and the aqueous layer was extracted with toluene (111 ml). The combined organic layer was washed with water (3×30 ml). The organic layer was dried over anhydrous magnesium sulfate and then the solvent was distilled off under reduced pressure to provide 18.9 g of the title compound (5) as colorless oil. Yield: 95.1%. The product was used in the subsequent reaction without purification.

IR (CHCl$_3$): 3619, 3502, 3020, 2974, 2937, 2872, 2818, 1623, 1460 cm$^{-1}$ $[\alpha]_D^{23.5}$+86.4° (c=1.00%, CH$_3$OH) (5) Step 3

Preparation of [(1R, 2R, 3R, 5S)-2-amino-10-norpinan-3-yl]ethanol benzoic acid salt (II')

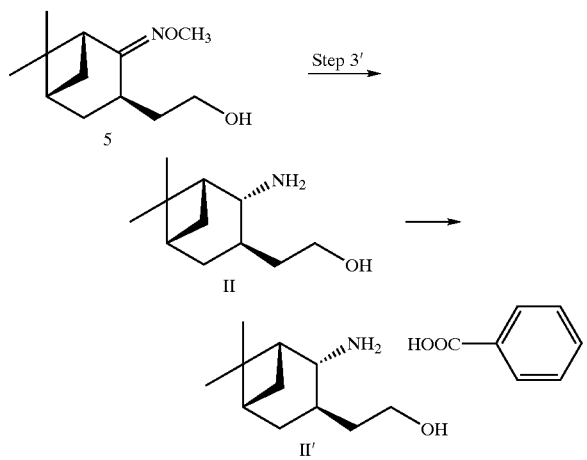

The compound (5) (9.63 g, 45.58 mmol) prepared in (4) was dissolved in toluene (33 ml) and n-propanol (72 ml). To the solution was added metal sodium (7.47 g, 325 mmol) in portions under reflux over 25 minutes. After 1 hour, additional metal sodium (1.15 g, 50 mmol) was added, and stirring was continued for 1 hour under reflux. The reaction mixture was cooled and then partitioned into two layers by adding ice water (39 ml) and toluene (95 ml). The aqueous layer was extracted with toluene (95 ml). The combined organic layer was washed with brine (3×95 ml) and dried over anhydrous magnesium sulfate, and the solvent was distilled off under reduced pressure to provide 8.4 g of the title compound (II) as colorless oil. The compound (II) 8.4 g (45.8 mmol) was dissolved in toluene (33.3 ml) and acetone (111 ml) and the solution was heated to 50° C. After adding a solution of benzoic acid (4.82 g, 39.47 mmol) in acetone (22.2 ml), the mixture was stirred at the same temperature for 1 hour. The deposited crystals were filtered and washed with cold acetone (33.3 ml) and dried to provide 9.155 g of colorless amino alcohol benzoic acid salt (III). Yield: 65.8%.

IR (Nujol): 3428, 2999, 2921, 2864, 2727, 2633, 2596, 2107, 1663, 1623, 1592, 1555, 1523, 1456, 1444 cm$^{-1}$ $[\alpha]_D^{23.5}$+27.1 (c=1.01%, CH$_3$OH), mp 181–183° C.

EXAMPLE 2

(1) Step 1

Preparation of [3-[(1R, 2R, 3R, 5 S)-3-(2-hydroxyethyl)-10-norpinan-2-yl]carbamoylbenzo[b]thiophen-5-yl]benzenesulfonate (7)

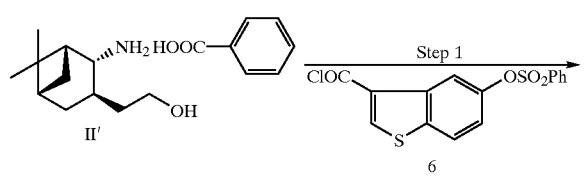

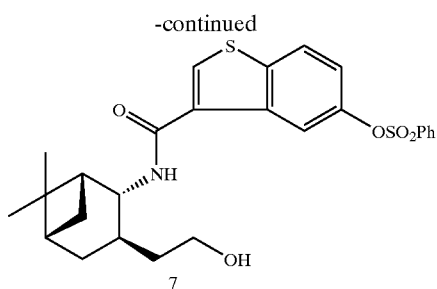

(+)-2-[(1R, 2R, 3R, 5S)-2-Amino-10-norpinan-3-yl]ethanol benzene sulfonic acid salt (II', 5.1 g, 16.7 mmol) prepared in Example 1 was suspended in water (10 ml). To the suspension was added 1 N HCl (17 ml) and the deposited benzoic acid was removed by extracting with ethyl acetate. The organic layer was washed with water (10 mL). To the combined aqueous layer was added 4 N sodium hydroxide (9.2 ml, 36.8 mmol) under ice-cooling, and a solution of 5-benzenesulfonyloxybenzo[b]thiophene-3-carbonyl chloride (6) (5.89 g, 16.7 mmol) prepared in Reference Example 2 in tetrahydrofuran (36 ml) was then added dropwise over 15 minutes with stirring. After stirring for another 1 hour at the same temperature, 1 N hydrochloric acid (4 ml) was added and extracted with ethyl acetate. The organic layer was washed with water, dried over anhydrous magnesium sulfate and then the solvent was distilled off under reduced pressure to provide 8.00 g (95.6%) of the title compound (7) as colorless amorphous.

$^1$H NMR δ(CDCl$_3$), 300 MHz; 0.96 (1H, d, J=9.9 Hz), 1.12 and 1.26 (each 3H, each s), 1.50–2.42 (9H, m), 3.69–3.82 (2H, m), 4.30 (1H, m), 6.21 (1H, d, J=8.1 Hz), 7.06 (1H, dd, J=2.4 and 8.7 Hz), 7.5–17.56 (2H, m), 7.67 (1H, m), 7.73 (1H, d, J=8.7 Hz), 7.85–7.88 (2H, m), 7.88 (1H, s), 8.06 (1H, d, J=2.4 Hz)

$[α]_D^{25}$ +35.7° (c=1.00%, CH$_3$OH)

(2) Step 2

Preparation of [3-[(1R, 2R, 3R, 5S)-3-formylmethyl-10-norpinan-2-yl]carbamoylbenzo[b]thiophen-5-yl]benzenesulfonate (8)

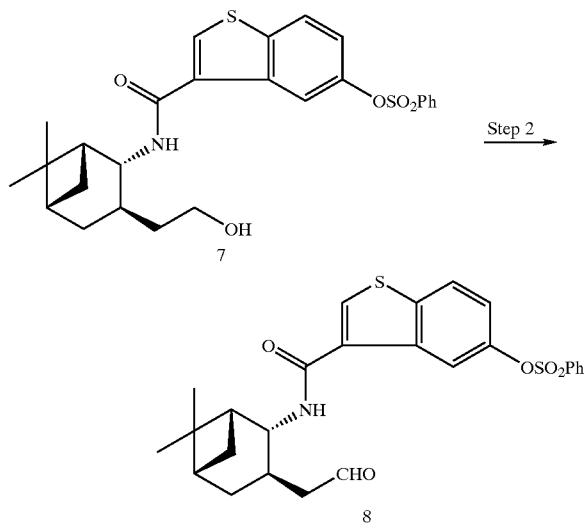

The compound (7) (9.72 g, 18.3 mmol) was dissolved in ethyl acetate (70 ml). To the solution were added TEMPO (2,2,6,6-tetramethylpiperidine-1-oxyl, 14.3 mg, 0.005 equivalent) and potassium bromide (218 mg, 0.1 equivalent). 0.41 N Aqueous sodium hypochlorite (45 ml of a solution adjusted to pH 9.5 with sodium hydrogen carbonate, 1 equivalent) was added dropwise over 3 minutes with stirring while maintaining the inner temperature at −1° C.–6° C. After 10 minutes at this temperature, the two layers were separated and the aqueous layer was extracted with ethyl acetate. The organic layer was washed with water, dried over anhydrous magnesium sulfate and then the solvent was distilled off under reduced pressure to provide 9.10 g (100%) of the title compound (8) as colorless amorphous.

IR (CHCl$_3$); 3443, 3093, 3066, 3030, 3016, 2925, 2871, 2828, 2729, 1720, 1655, 1599, 1558, 1513, 1377 cm$^{-1}$ $^1$H NMR δ(CDCl$_3$), 300 MHz; 0.97 (1H, d, J=10.2 Hz), 1.17 and 1.28 (each 3H, each s), 1.46 (1H, m), 2.03 (1H, m), 2.22 (1H, m), 2.36–2.60 (3H, m), 2.69 (1H, ddd, J=1.2, 8.7 and 17.4 Hz), 3.14 (1H, dd, J=4.5 and 17.4 Hz), 4.28 (1H, m), 6.18 (1H, d, J=8.1 Hz), 7.09 (1H, dd, J=2.4 and 8.7 Hz), 7.50–7.55 (2H, m), 7.67 (1H, m), 7.75 (1H, d, J=8.7 Hz), 7.85–7.89 (2H, m), 7.89 (1H, s), 8.03 (1H, d, J=2.4 Hz), 9.80 (1H, d, J=1.2 Hz)

$[α]_D^{23}$ +31.8° (c=1.00%, CH$_3$OH)

(3) Step 3

Preparation of (5Z)-7-[(1R, 2R, 3S, 5S)-2-(5-benzenesulfonyloxybenzo[b]thiophen-3-ylcarbonylamino)-10-norpinan-3-yl]-5-heptenoic acid (9)

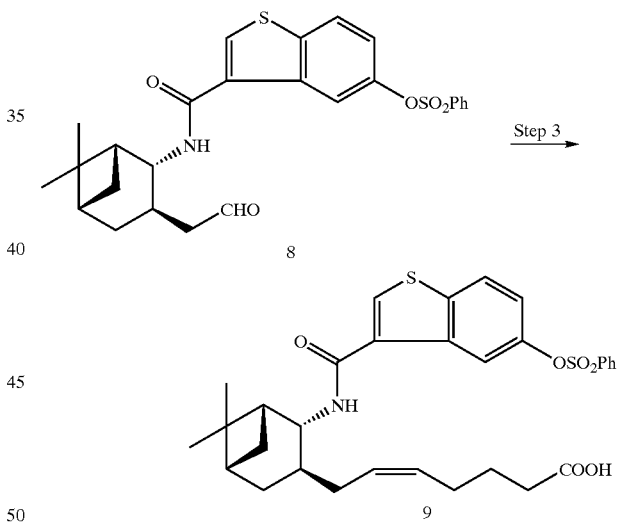

4-Carboxybutyltriphenylphosphonium bromide (12.17 g, 27.5 mmol) and potassium t-butoxide (7.19 g, 64.1 mmol) were suspended in tetrahydrofuran (64 ml) and the mixture was stirred under ice-cooling for 1 hour. To the reaction mixture was added a solution of compound (8) (9.11 g, 18.3 mmol) prepared in above (2) in tetrahydrofuran (27 ml) over 15 minutes, and stirring was continued for 2 hours at the same temperature. The reaction was diluted with water (80 ml) and washed with toluene (2×105 ml). After the aqueous layer was adjusted to pH 8.1 with 5 N hydrochloric acid (4.8 ml), anhydrous calcium chloride (8.1 g, 73 mmol) dissolved in water (16 ml) was added and the mixture was extracted with ethyl acetate (2×100 ml). To the organic layer was added water (100 ml) and the aqueous layer was adjusted to below pH 2 with 5 N hydrochloric acid and extracted with ethyl acetate. The organic layer was washed with water, dried over anhydrous magnesium sulfate and then the solvent was distilled off under reduced pressure to provide 11.06 g of the compound (9), which was used without purification.

(4) Step 4

Preparation of (5Z)-7-[(1R, 2R, 3S, 5S)-2-(5-hydroxybenzo[b]thiophen-3-ylcarbonylamino)-10-norpinan-3-yl]-5-heptenoic acid (10) (Compound A))

The compound (9) (11.06 g, 18.3 mmol) prepared in above (3) was dissolved in dimethyl sulfoxide (22 ml). To the solution was added 4 N sodium hydroxide (27.5 ml), and the mixture was heated at 55° C. for 2 hours with stirring. The reaction mixture was diluted with water (130 ml) and washed with toluene (2×65 ml). The aqueous layer was acidified with 5 N hydrochloric acid and then extracted with ethyl acetate. The organic layer was washed with water, dried over anhydrous magnesium sulfate and then the solvent was distilled off under reduced pressure to provide 8.26 g of the crude objective compound (10). The product was dissolved in methanol (40 ml) and water (16 ml), and the mixture was seeded and gradually cooled with stirring. The deposited crystals were filtered and washed with water: methanol (2:5) to provide 6.35 g of the objective compound (10). Yield: 78.6%. The crystals were dissolved in methanol (40 ml), and water (12 ml) was added with stirring over 7 minutes. After adding seeds, the solution was continuously stirred at 25° C. for 1 hour. Additional water (7 ml) was added over 40 minutes and stirring was continued for 1.5 hours at 25° C. The deposited crystals were filtered and washed with water: methanol (3:5) (8 ml) to provide 6.14 g of the almost colorless objective compound (10). Yield: 76.0%, mp 145–146° C.

IR (Nujol); 3313, 3096, 3059, 3001, 1717, 1627, 1603, 1548, 1469, 1440 cm$^{-1}$ $^1$H NMR δ(CDCl$_3$), 300 MHz; 1.02 (1H, d, J=10.2 Hz), 1.12 and 1.24 (each 3H, each s), 1.56–2.55 (14H, m), 4.29 (1H, m), 5.32–5.51 (2H, m), 6.20 (1H, d, J=9.3 Hz), 7.01 (1H, dd, J=2.4 and 9.0 Hz), 7.66 (1H, d, J=9.0 Hz), 7.69 (1H, s), 8.03 (1H, d, J=2.4 Hz)

$[\alpha]_D^{24}$+50.7° (c=1.01, CH$_3$OH)

| | Elemental Analyses for C$_{25}$H$_{31}$NO$_4$S |
|---|---|
| Calculated (%): | C, 68.00; H, 7.08; N, 3.17; S, 7.26 |
| Found (%): | C, 67.84; H, 7.08; N, 3.24; S, 7.31 |

What is claimed is:

1. A process for preparing an amino alcohol of the formula (II):

II or a salt thereof, which comprises converting a compound of formula (II-2):

II-2 wherein R$^2$ is alkyl and R$^3$ is hydrogen or alkyl, into an alcohol of formula (II-3):

II-3 wherein R$^3$ is as defined above; and reducing the alcohol with a metal sodium-alcohol or a reducing agent-Lewis acid system.

* * * * *